(12) United States Patent
Erdman

(10) Patent No.: US 6,472,535 B1
(45) Date of Patent: Oct. 29, 2002

(54) OXIDATIVE HYDROLYSIS OF HETEROAROMATIC THIONES

(75) Inventor: David T. Erdman, Liberty, MO (US)

(73) Assignee: Bayer Corporation, Pittsburgh, PA (US)

( * ) Notice: Subject to any disclaimer, the term of this patent is extended or adjusted under 35 U.S.C. 154(b) by 0 days.

(21) Appl. No.: 09/970,387

(22) Filed: Oct. 2, 2001

(51) Int. Cl.$^7$ .............................................. C07D 249/12
(52) U.S. Cl. ................................................... 548/263.2
(58) Field of Search ...................... 548/263.2

(56) References Cited

U.S. PATENT DOCUMENTS

| | | | |
|---|---|---|---|
| 3,780,052 A | 12/1973 | Cebalo et al. | 260/308 C |
| 3,884,910 A | 5/1975 | Pilgram | 260/240 G |
| 5,475,115 A | 12/1995 | Linker et al. | 548/263.2 |
| 5,508,420 A | 4/1996 | Haas et al. | 548/263.2 |
| 5,639,891 A | 6/1997 | Linker et al. | 543/264.2 |
| 5,688,963 A | 11/1997 | Haas et al. | 548/263.2 |
| 5,728,651 A | 3/1998 | Hong et al. | 504/246 |
| 5,739,349 A | 4/1998 | Linker et al. | 548/264.6 |

*Primary Examiner*—T. A. Solola
*Assistant Examiner*—Rebecca Anderson
(74) *Attorney, Agent, or Firm*—Joseph C. Gil; Raymond J. Harmuth

(57) ABSTRACT

A process for preparing a triazolinone includes the step of reacting a triazolinethione with an oxidant at a temperature range of from about 60° C. to about 100° C. in the presence of a base.

17 Claims, No Drawings

OXIDATIVE HYDROLYSIS OF HETEROAROMATIC THIONES

FIELD OF THE INVENTION

The invention relates to processes for the preparation of heteroaromatic thiones. More particularly invention relates to processes for the preparation of triazolinones comprising the step of reacting a triazolinethione with an oxidant in the presence of a base.

BACKGROUND OF THE INVENTION

Heteroaromatic thiones such as triazolinones may be used as herbicides and/or pesticides, or as useful intermediates in the production of herbicides and/or pesticides.

Cebalo et al., U.S. Pat. No. 3,780,052, disclose that substituted triazolinones may be obtained when the corresponding triazolinethiones are reacted with an alkylating agent in the presence of an acid-binding agent, and the resulting alkylthiotriazole derivative is then heated with hydrogen peroxide in the presence of acid.

Linker et al., U.S. Pat. Nos. 5,475,115; 5,639,891 and 5,739,349, disclose that triazolinones may be prepared by reacting alkylsulphonyltriazole derivatives with an aqueous alkali metal hydroxide solution at temperatures between 0° C. and 100° C. under atmospheric pressure to obtain a product, and then acidifying the product.

Haas, et al., U.S. Pat. Nos. 5,508,420 and 5,688,963, disclose that triazolinones may be prepared by reacting triazolinethiones with oxidants at a temperature of from about 0° C. to about 100° C. to obtain triazolesulphonic acids, and reacting the triazolesulphonic acids with water at a temperature of from about 20° C. to about 120° C., optionally in the presence of an acid.

Hong et al., U.S. Pat. No. 5,728,651, disclose the reaction of hydrazones and diphenylphosphoryl azide followed by a ring cyclization to obtain triazolinones.

Some prior art processes require an acidic oxidation of a triazolthione followed by an alkaline hydrolysis, while other prior art processes require an alkaline oxidation of a triazolthione followed by an acidic hydrolysis. Unfortunately changing from acidic to basic, or basic to acidic, conditions may result in the formation of undesirable salts. Further, prior art processes such as the cleavage of triazolesulphonate under acidic conditions require long reflux times.

Thus there is a need of a facile method of synthesizing heteroaromatic thiones, such as triazolinones.

SUMMARY OF THE INVENTION

Accordingly, it is an object of the present invention to obviate problems of the prior art.

It is a further object of the present invention to provide processes for the preparation of triazolinones which do not require a change from acidic to basic, or basic to acidic, conditions.

It is a further object of the present invention to provide processes for the preparation of triazolinones which do not require long reflux times. As used herein "long reflux times" refer to reflux times of greater than 10 hours.

These and additional objects are provided by the processes of the invention.

According to one aspect of the invention there are provided processes for preparing a heteroaromatic thione, preferably a triazolinone, which include the step of reacting a triazolinethione with an oxidant in the presence of a base. The processes may be performed at a temperature in the range of from about 60° C. to about 100° C.

According to another aspect of the invention there are provided processes for preparing a triazolinone of the formula:

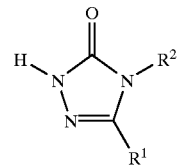

wherein $R^1$ represents alkyl having 1 to 6 carbon atoms which is optionally substituted by halogen, cyano or $C_1$–$C_4$ alkoxy, or represents cycloalkyl having 3 to 6 carbon atoms which is optionally substituted by halogen, cyano or $C_1$–$C_4$-alkyl, and $R^2$ represents amino, or a radical selected from the group consisting of alkyl, alkenyl, alkinyl, alkoxy, alkylamino or dialkylamino, each of which has up to 6 carbon atoms in the alkyl, alkenyl or alkinyl groups and each of which is optionally substituted by halogen, cyano or $C_1$–$C_4$-alkoxy, or represents a radical selected from the group consisting of $C_3$–$C_6$-cycloalkyl, $C_3$–$C_6$-cycloalkyl-$C_1$–$C_2$-alkyl or phenyl, each of which is optionally substituted by halogen, cyano, $C_1$–$C_4$-alkyl, $C_1$–$C_4$-alkoxy or $C_1$–$C_4$-alkoxycarbonyl. The process utilizes a triazolinethione of the formula:

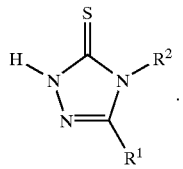

The process comprises the step of reacting the triazolinethione with an oxidant at a temperature range of from about 60° C. to about 100° C. in the presence of a base for a time of from about 1 hour to about 6 hours, at a molar ratio of triazolinethione to oxidant to base of from about 1:5:4 to about 1:20:10; or comprises the step of mixing a solvent, a base and the triazolinethione, adding an oxidant and heating the resulting reaction mixture.

These and additional aspects, objects and advantages of the invention are more fully described in the following detailed description.

DETAILED DESCRIPTION

Processes in accordance with the present invention may be used to produce heteroaromatic thiones, particularly triazolinones. Triazolinones may be used as herbicides and/or pesticides and/or pharmaceuticals, or as useful intermediates in the production of herbicides and/or pesticides and/or pharmaceuticals.

Suitable triazolinones include 1,2,4 triazol-5-thiones. In one embodiment of the reaction the triazolinone has the formula:

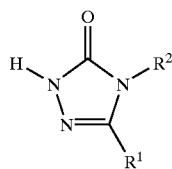

wherein $R^1$ represents an alkyl having 1 to 6 carbon atoms which may be unsubstituted or substituted by halogen, cyano or $C_1$–$C_4$-alkoxy, or represents a cycloalkyl having 3 to 6 carbon atoms which may be unsubstituted or substituted by halogen, cyano or $C_1$–$C_4$-alkyl; and $R^2$ represents amino, or represents a radical selected from the group consisting of alkyl, alkenyl, alkinyl, alkoxy, alkylamino or dialkylamino, each of which has up to 6 carbon atoms in the alkyl, alkenyl or alkinyl groups and each of which may be unsubstituted or substituted by halogen, cyano or $C_1$–$C_4$-alkoxy, or represents a radical selected from the group consisting of $C_3$–$C_6$-cycloalkyl, $C_3$–$C_6$-cycloalkyl-$C_1$–$C_2$-alkyl or phenyl, each of which may be unsubstituted or substituted by halogen, cyano, $C_1$–$C_4$-alkyl, $C_1$–$C_4$-alkoxy or $C_1$–$C_4$-alkoxycarbonyl.

In one embodiment $R^1$ represents methyl, ethyl, n- or i-propyl, or n-, i- or s-butyl, each of which may be unsubstituted or substituted by fluorine, chlorine, bromine, cyano, methoxy or ethoxy, or represents cyclopropyl, cyclopropylmethyl, cyclobutyl, cyclopentyl or cyclohexyl, each of which may be unsubstituted or substituted by fluorine, chlorine, bromine, cyano or methyl; while in another embodiment $R^1$ represents methyl, ethyl, n- or i-propyl, cyclopropyl or cyclopropylmethyl, each of which is mono-, di-, tri-, tetra-, penta-, hexa- or heptasubstituted by fluorine and/or chlorine.

In one embodiment $R^2$ represents amino, a radical selected from the group consisting of methyl, ethyl, n- or i-propyl, n-, i- or s-butyl, allyl, propargyl, methoxy, ethoxy, n- or i-propoxy, n-, i- or s-butoxy, methylamino, ethylamino, n- or i-propylamino, n-, i- or s-butylamino, dimethylamino or diethylamino, each of which may be unsubstituted or substituted by fluorine, chlorine, cyano, methoxy or ethoxy, or represents a radical selected from the group consisting of cyclopropyl, cyclobutyl, cyclopentyl or cyclohexyl or phenyl, each of which may be unsubstituted or substituted by fluorine, chlorine, bromine, cyano, methyl, ethyl, n- or i-propyl, methoxycarbonyl or ethoxycarbonyl; while in another embodiment $R^2$ represents methyl, ethyl, n- or i-propyl, methoxy, ethoxy, methylamino, ethylamino, dimethylamino, cyclopropyl, phenyl or tolyl.

In accordance with one embodiment of the invention, a triazolinone of the formula:

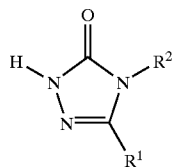

is formed by reacting a triazolinethione of the formula:

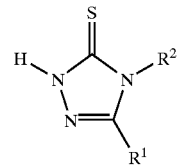

and an oxidant in the presence of base. The reaction may occur at a temperature in the range of from about 60° C. to about 100° C., preferably from about 60° C. to about 90° C., more preferably from about 80° C. to about 90° C., and for a time of no more than about 10 hours, preferably less than 10 hours, such as from about 1 hour to about 6 hours, preferably from about 2 to about 3 hours. In one embodiment the reaction occurs for a time of no more than 4 hours, preferably no more than 3 hours. The molar ratio of triazolinethione to oxidant to base of from about 1:5:4 to about 1:20:10, preferably from about 1:4:4 to about 1:10:6. In accordance with another embodiment of the invention a triazolinone of the formula:

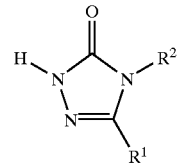

is prepared by first mixing solvent, base and a triazolinethione of the formula:

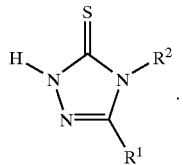

An oxidant is then added to the solvent, base and triazolinethione to form a reaction mixture and the reaction mixture is heated. The mole ratio of oxidant to triazolinethione is from about 20:1 to about 4:1, preferably about 5:1, while the mole ratio of base to triazolinethione is from about 4:1 to about 10:1, preferably about 5:1.

In one embodiment of the reaction, the step of adding the oxidant and the step of heating the reaction mixture occurs at the same temperature, while in another embodiment the steps occur at different temperatures. The step of heating the reaction mixture may occur at a higher temperature than the step of adding the oxidant.

For example, the step of adding an oxidant may occur at a temperature in the range of from about 30° C. to about 70° C., preferably about 50° C. to about 60° C., while the step of heating the reaction mixture may comprise heating the reaction mixture at a temperature in the range of from about 60° C. to about 100° C., preferably from about 90° C. to about 100° C. After the reaction mixture is heated to the desired temperature it may be maintained at the desired temperature of a period of time of no more than about 10 hours, preferably less than 10 hours, such as from about 1 hour to about 6 hours, preferably from about 2 to about 3 hours. In one embodiment the reaction mixture is maintained at the desired temperature for a time of no more than 4 hours, preferably no more than 3 hours.

The step of adding an oxidant and the step of heating the reaction mixture may be performed at any pressure at which the desired reaction occurs. If desired, a slight vacuum may be employed in order to avoid a high concentration of oxygen in the reaction vessel.

While not being bound by theory, the reaction is believed to proceed as follows:

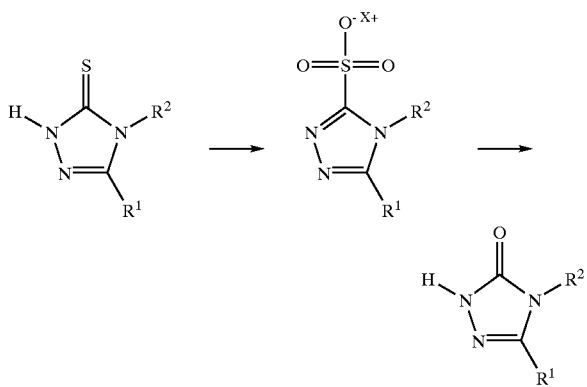

As used herein, "oxidants" is intended to refer to compounds capable of oxidizing triazolinones. In one embodiment of the invention the oxidant is hydrogen peroxide.

Bases include inorganic or organic bases such as, for example, hydroxides and alcoholates of alkaline earth metals or alkali metals. Generally a strong base is preferred. Preferred bases include sodium hydroxide, potassium hydroxide, sodium methylate, sodium ethylate, potassium tert-butylate, and combinations thereof. In one preferred embodiment the base is a hydroxide, particularly sodium hydroxide.

The pH of the mixture of solvent, base, triazolinethione and oxidant is generally in the basic range, such as from about 10 to about 14, preferably from about 12 to about 14.

The processes according to the invention may be carried out using a diluent. Suitable diluents are, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane; ethers, such as diethyl ether, diisopropyl ether, dioxane, tetrahydrofuran or ethylene glycol dimethyl ether or ethylene glycol diethyl ether; alcohols, such as methanol, ethanol, n- or i- propanol, ethylene glycol monomethyl ether, ethylene glycol monoethyl ether, diethylene glycol monomethyl ether, diethylene glycol monoethyl ether, their mixtures with water, or pure water.

The product may be purified from the reaction mixture using any suitable method. For example, the reaction mixture may be repeatedly extracted using an organic solvent which is substantially immiscible with water, such as, for example, methylene chloride, and the combined organic extraction solutions dried and filtered. After the solvent has carefully been removed from the filtrate by distillation, the product is obtained as the residue.

Throughout the example and the present specification, parts and percentages are by weight unless otherwise specified. The following example is illustrative only and is not intended to limit the scope of the methods of the invention as defined by the claims.

EXAMPLE

In a two-liter cylinder reactor fitted with a condenser and a glass stir rod having TEFLON™ paddles is placed about 600 ml distilled water, about 192 g of a 50%, by weight, sodium hydroxide solution and about 96 g of 3-trifluoromethyl-4-methyl-1,2,4 triazol-5-thione. The ingredients are mixed and the resulted mixture heated to about 50° C.

About 272 g of a solution of 30% hydrogen peroxide is added while maintaining the temperature of the reactor in the range of from about 50 to about 60° C. The initial addition of the peroxide results in an exothermic reaction, thus the peroxide is generally added slowly while the reactor is cooled in order to maintain the desired temperature.

The reactor is then heated and about 272 g of additional 30% hydrogen peroxide is added. The reactor is allowed to reach a temperature of about 90° C. After the addition of the total hydrogen peroxide, the reactor is heated at reflux for about one hour. Water is removed by distillation and dimethyl sulfoxide (DMSO) is added. The resulting slurry is filtered and the solids washed with DMSO. Yield is about 80%. The anion of the product is dissolved in the DMSO. The product may be further concentrated or purified by any suitable method.

Additional embodiments and modifications within the scope of the claimed invention will be apparent to one of ordinary skill in the art. Accordingly, the scope of the present invention shall be considered in terms of the following claims, and is understood not to be limited to the details of the methods described in the specification.

What is claimed is:

1. A process for preparing a triazolinone of the formula:

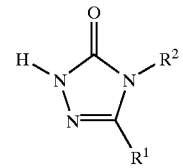

wherein
  $R^1$ represents alkyl having 1 to 6 carbon atoms which is optionally substituted by halogen, cyano or $C_1$–$C_4$ alkoxy, or represents cycloalkyl having 3 to 6 carbon atoms which is optionally substituted by halogen, cyano or $C_1$–$C_4$-alkyl, and
  $R^2$ represents amino, or a radical selected from the group consisting of alkyl, alkenyl, alkinyl, alkoxy, alkylamino or dialkylamino, each or which has up to 6 carbon atoms in the alkyl, alkenyl or alkinyl groups and each of which is optionally substituted by halogen, cyano or $C_1$–$C_4$-alkoxy, or represents a radical selected from the group consisting of $C_3$–$C_6$-cycloalkyl, $C_3$–$C_6$-cycloalkyl-$C_1$–$C_2$-alkyl or phenyl, each of which is optionally substituted by halogen, cyano, $C_1$–$C_4$-alkyl, $C_1$–$C_4$-alkoxy or $C_1$–$C_4$-alkoxycarbonyl,
comprising the steps of mixing a triazolinethione of the formula

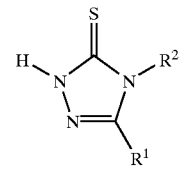

wherein $R^1$ and $R^2$ are as defined above in this claim 1,
  with an oxidant at a temperature range of from about 60° C. to about 100° C. in the presence of a base; and reacting the mixture of said triazolinethione, said oxidant and said base for a time of from about 1 hour to about 6 hours, at a molar ratio of triazolinethione to oxidant to base of from about 1:5:4 to about 1:20:10, wherein said mixture of said triazolinethione, said oxidant and said base has a basic pH in the range of about 10 to 14 and wherein said triazolinone is formed without changing said mixture to an acidic pH.

2. A process according to claim 1, wherein the oxidant is a peroxide.

3. A process according to claim 2, wherein the peroxide is hydrogen peroxide.

4. A process according to claim 1, wherein the base is an alkali metal hydroxide.

5. A process according to claim 1, wherein the triazolinethione is 3-trifluoromethyl-4-methyl-1,2,4 triazol-5-thione.

6. A process according to claim 1, wherein the molar ratio of triazolinethione to oxidant to base is about 1:10:5.

7. A process according to claim 1, wherein $R^1$ represents methyl, ethyl, n- or i-propyl, or n-, i- or s-butyl, each of which may be unsubstituted or substituted by fluorine, chlorine, bromine, cyano, methoxy or ethoxy, or represents cyclopropyl, cyclopropylmethyl, cyclobutyl, cyclopentyl or cyclohexyl, each of which may be unsubstituted or substituted by fluorine, chlorine, bromine, cyano or methyl.

8. A process according to claim 1, wherein $R^2$ represents amino, a radical selected from the group consisting of methyl, ethyl, n- or i-propyl, n-, i- or s-butyl, allyl, propargyl, methoxy, ethoxy, n- or i-propoxy, n-, i- or s-butoxy, methylamino, ethylamino, n- or i-propylamino, n-, i- or s-butylamino, dimethylamino or diethylamino, each of which may be unsubstituted or substituted by fluorine, chlorine, cyano, methoxy or ethoxy, or represents a radical selected from the group consisting of cyclopropyl, cyclobutyl, cyclopentyl or cyclohexyl or phenyl, each of which may be unsubstituted or substituted by fluorine, chlorine, bromine, cyano, methyl, ethyl, n- or i-propyl, methoxycarbonyl or ethoxycarbonyl.

9. A process for preparing a triazolinone of the formula:

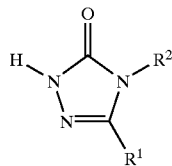

wherein
$R^1$ represents alkyl having 1 to 6 carbon atoms which is optionally substituted by halogen, cyano or $C_1$–$C_4$-alkoxy, or represents cycloalkyl having 3 to 6 carbon atoms which is optionally substituted by halogen, cyano or $C_1$–$C_4$-alkyl, and $R^2$ represents amino, or a radical selected from the group consisting of alkyl, alkenyl, alkinyl, alkoxy, alkylamino or dialkylamino, each or which has up to 6 carbon atoms in the alkyl, alkenyl or alkinyl groups and each of which is optionally substituted by halogen, cyano or $C_1$–$C_4$-alkoxy, or represents a radical selected from the group consisting of $C_3$–$C_6$-cycloalkyl, $C_3$–$C_6$-cycloalkyl-$C_1$–$C_2$-alkyl or phenyl, each of which is optionally substituted by halogen, cyano, $C_1$–$C_4$-alkyl, $C_1$–$C_4$-alkoxy or $C_1$–$C_4$-alkoxycarbonyl, comprising the steps of (a) mixing solvent, base and a triazolinethione of the formula

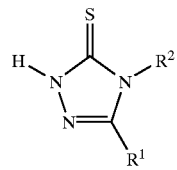

wherein $R^1$ and $R^2$ are as defined above in this claim 9, (b) adding an oxidant to the solvent, base and triazolinethione to form a reaction mixture, and (c) heating the reaction mixture, wherein said reaction mixture of said solvent, said base, said triazolinethione, and said oxidant has a basic pH in the range of about 10 to 14 and wherein said triazolinone is formed without changing said reaction mixture to an acidic pH.

10. A process according to claim 9, wherein solvent comprises water.

11. A process according to claim 9, wherein the mole ratio of oxidant to triazolinethione is from about 20:1 to about 5:1.

12. A process according to claim 9, wherein the mole ratio of base to triazolinethione is from about 4:1 to about 10:1.

13. A process according to claim 9, the step of adding an oxidant occurs at a temperature in the range of from about 30° C. to about 70° C.

14. A process according to claim 9, the step of heating the reaction mixture comprises heating the reaction mixture at a temperature in the range of from about 60° C. to about 100° C.

15. A process according to claim 9, wherein the process further comprises the step of maintaining the reaction mixture at the temperature in the range of from about 60° C. to about 100° C. for a period of time of from about 1 to about 6 hours.

16. A process according to claim 9, wherein $R^1$ represents methyl, ethyl, n- or i-propyl, or n-, i- or s-butyl, each of which may be unsubstituted or substituted by fluorine, chlorine, bromine, cyano, methoxy or ethoxy, or represents cyclopropyl, cyclopropylmethyl, cyclobutyl, cyclopentyl or cyclohexyl, each of which may be unsubstituted or substituted by fluorine, chlorine, bromine, cyano or methyl.

17. A process according to claim 9, wherein $R^2$ represents amino, a radical selected from the group consisting of methyl, ethyl, n- or i-propyl, n-, i- or s-butyl, allyl, propargyl, methoxy, ethoxy, n- or i-propoxy, n-, i- or s-butoxy, methylamino, ethylamino, n- or i-propylamino, n-, i- or s-butylamino, dimethylamino or diethylamino, each of which may be unsubstituted or substituted by fluorine, chlorine, cyano, methoxy or ethoxy, or represents a radical selected from the group consisting of cyclopropyl, cyclobutyl, cyclopentyl or cyclohexyl or phenyl, each of which may be unsubstituted or substituted by fluorine, chlorine, bromine, cyano, methyl, ethyl, n- or i-propyl, methoxycarbonyl or ethoxycarbonyl.

* * * * *